(12) United States Patent
Trocki et al.

(10) Patent No.: US 7,475,701 B2
(45) Date of Patent: Jan. 13, 2009

(54) VALVE SYSTEMS AND INJECTOR SYSTEM INCLUDING SUCH VALVE SYSTEMS

(75) Inventors: Mark Trocki, Cheswick, PA (US); David M. Reilly, Glenshaw, PA (US)

(73) Assignee: MEDRAD, Inc., Indianola, PA (US)

( * ) Notice: Subject to any disclaimer, the term of this patent is extended or adjusted under 35 U.S.C. 154(b) by 212 days.

(21) Appl. No.: 11/420,094

(22) Filed: May 24, 2006

(65) Prior Publication Data
US 2007/0272311 A1  Nov. 29, 2007

(51) Int. Cl.
*F16K 11/00* (2006.01)
*F16K 7/12* (2006.01)
(52) U.S. Cl. ............... 137/112; 137/114; 137/512.4
(58) Field of Classification Search .......... 137/102, 137/111, 112, 113, 114, 512.4
See application file for complete search history.

(56) References Cited

U.S. PATENT DOCUMENTS

| | | | |
|---|---|---|---|
| 2,987,076 A | 6/1961 | Alderman | |
| 3,021,868 A | 2/1962 | Kovach | |
| 3,779,267 A * | 12/1973 | Cowan | ............. 137/111 |
| 4,006,736 A | 2/1977 | Kranys et al. | |
| 4,191,203 A * | 3/1980 | Panigati | ............. 137/112 |
| 4,237,880 A * | 12/1980 | Genese | ............. 604/81 |
| 4,246,932 A | 1/1981 | Raines | |
| 4,677,980 A | 7/1987 | Reilly et al. | |
| 4,729,401 A | 3/1988 | Raines | |
| 4,816,083 A | 3/1989 | Bangyan | |
| 5,176,658 A * | 1/1993 | Ranford | ............. 137/102 |
| 5,383,858 A | 1/1995 | Reilly et al. | |
| 5,494,036 A | 2/1996 | Uber, III et al. | |
| 6,083,194 A * | 7/2000 | Lopez | ............. 604/28 |
| 6,257,268 B1 * | 7/2001 | Hope et al. | ............. 137/112 |
| 2004/0064041 A1 | 4/2004 | Lazzaro et al. | |

OTHER PUBLICATIONS

International Search Report issued in corresponding International Application PCT/US07/68458.

* cited by examiner

*Primary Examiner*—Stephen M Hepperle
(74) *Attorney, Agent, or Firm*—Gregory Bradley; Henry Bartony, Jr.

(57) ABSTRACT

A valve system for use in a system including a first source of a first pressurized fluid and a second source of a second pressurized fluid includes a valve housing including a first inlet port adapted to be placed in fluid connection with the first source, a second inlet port adapted to be placed in fluid connection with the second source and an outlet port. The valve system further includes a backflow prevention system to prevent flow of the first pressurized fluid through the second inlet and to prevent flow of the second pressurized fluid through the first inlet port. The valve system is adapted to provide a fluid path between at least the first inlet port and the outlet port to enable fluid to be drawn from the outlet port to the first inlet port. Several of the valve systems of the present invention provide for flow from the first inlet port to the outlet port and concurrent flow from the second inlet port to the outlet port.

12 Claims, 14 Drawing Sheets

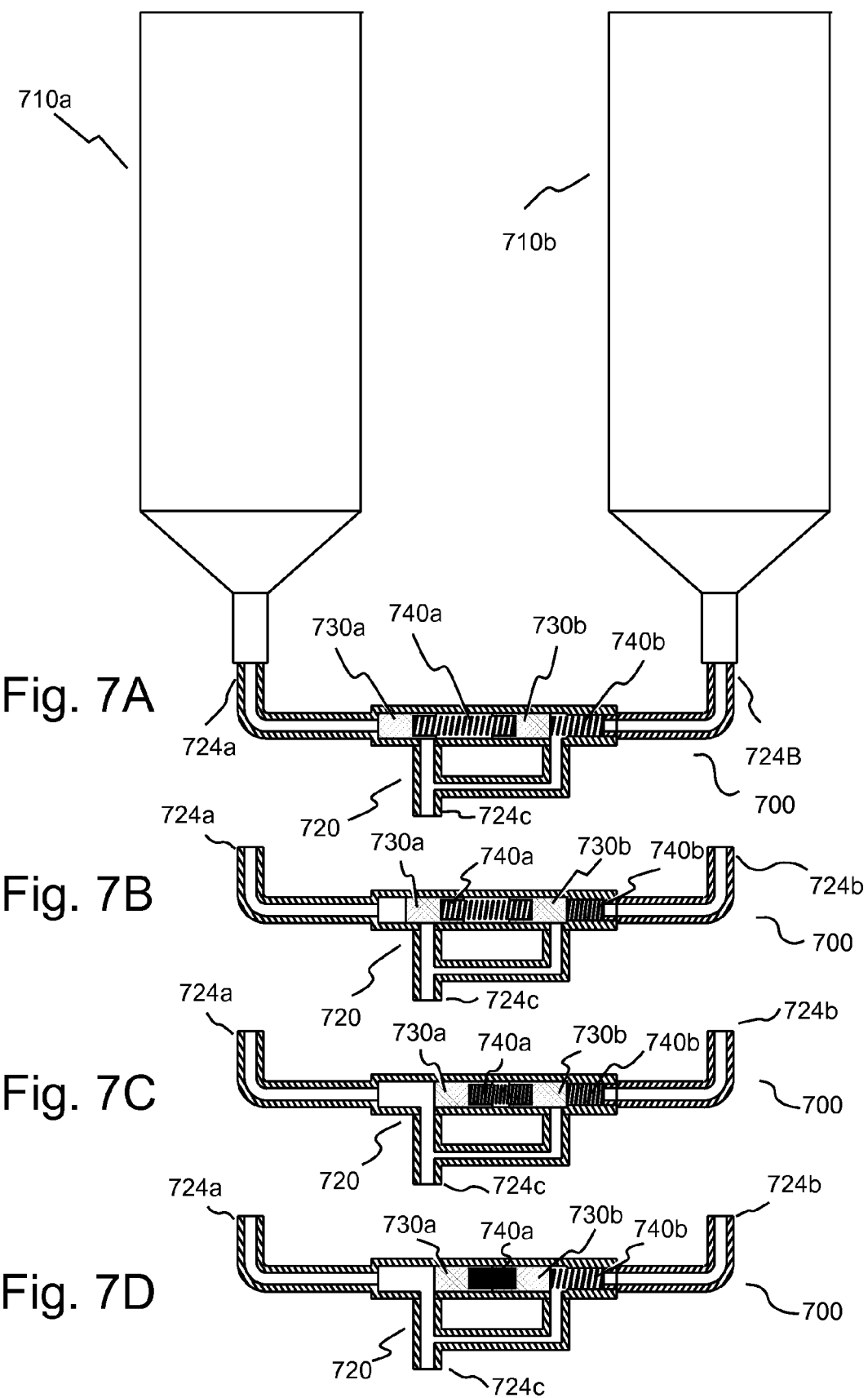

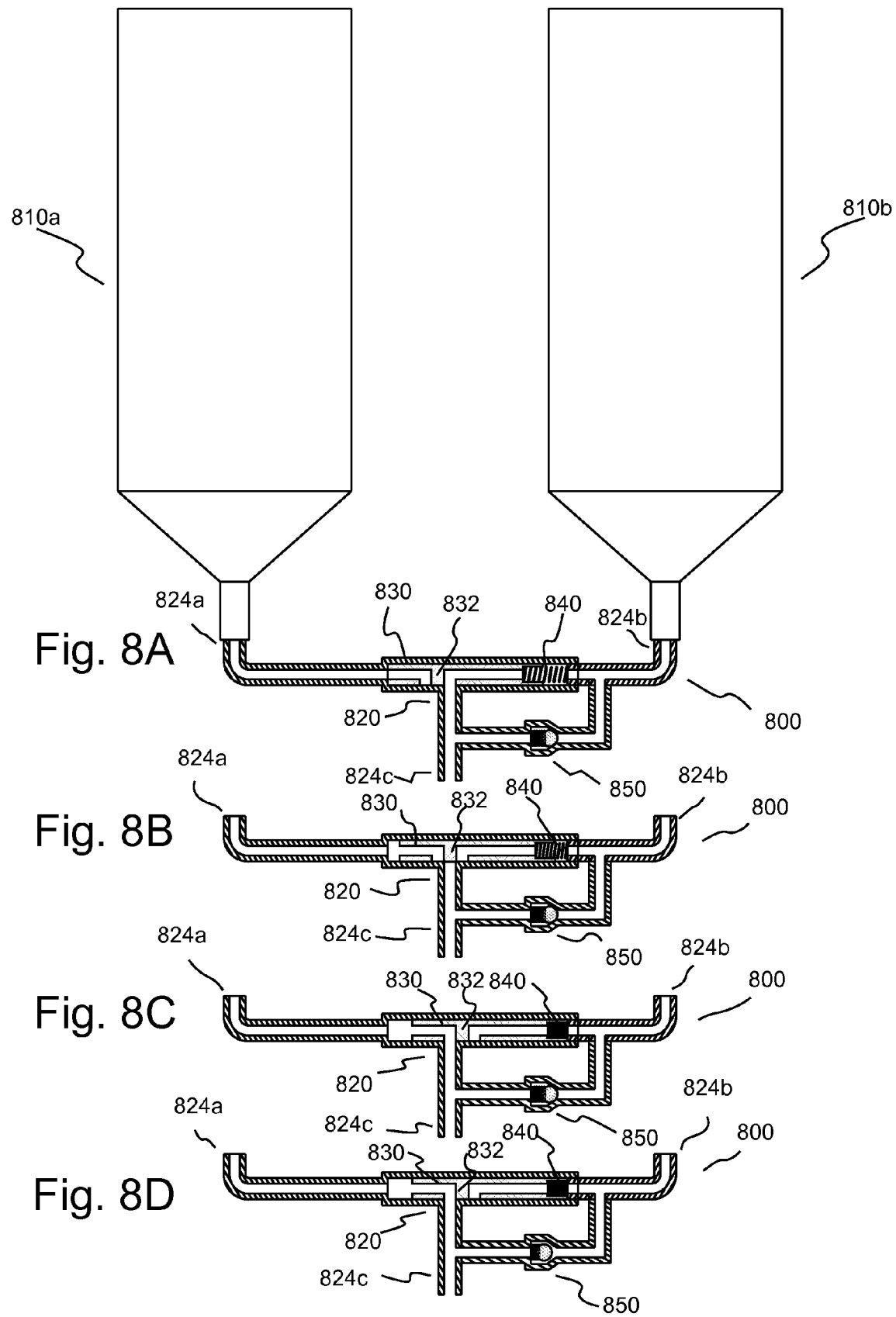

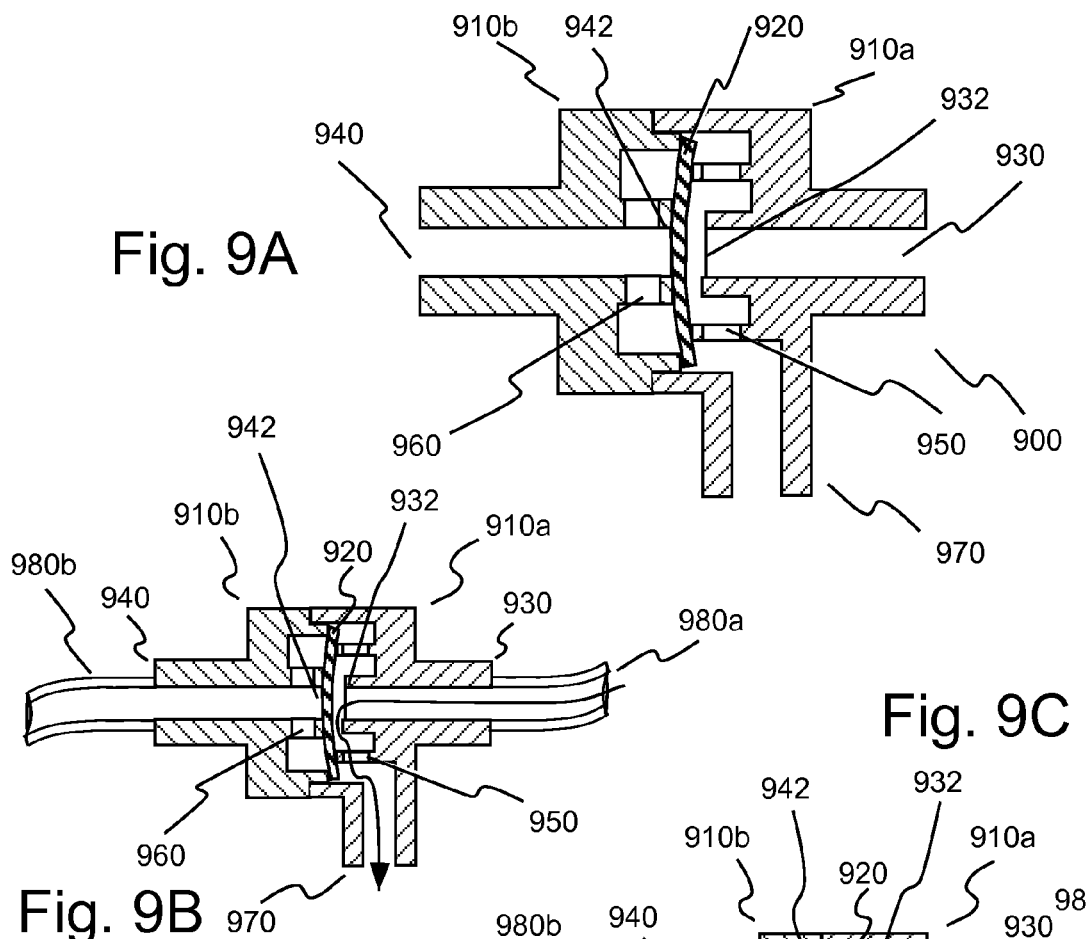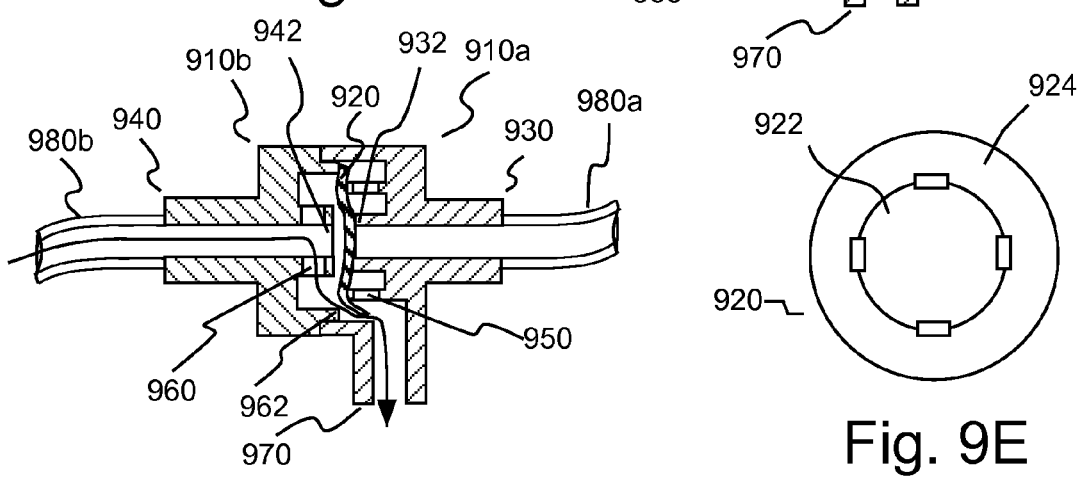

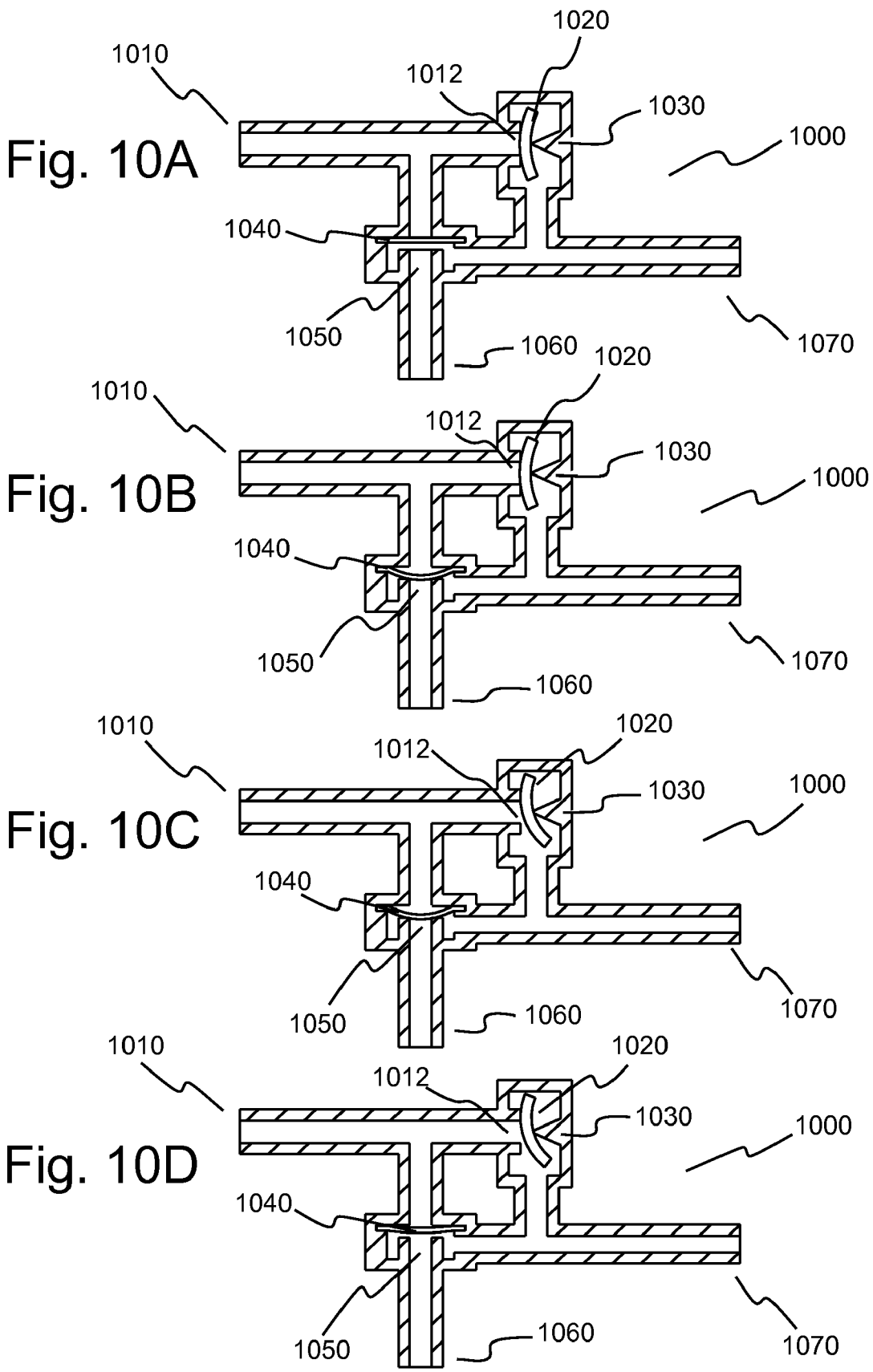

VALVE SYSTEMS AND INJECTOR SYSTEM INCLUDING SUCH VALVE SYSTEMS

BACKGROUND OF THE INVENTION

The present invention relates generally to valve systems and injector systems including such valve systems and, particularly, to valve systems for use in injecting multiple fluids and to injectors systems including such valve systems.

In many medical procedures, such as drug delivery, it is desirable to inject a fluid into a patient. Likewise, numerous types of contrast media (often referred to simply as contrast) are injected into a patient for many diagnostic and therapeutic imaging procedures. For example, contrast media are used in diagnostic procedures such as X-ray procedures (including, for example, angiography, venography and urography), computed tomography (CT) scanning, magnetic resonance imaging (MRI), and ultrasonic imaging. Contrast media are also used during therapeutic procedures, including, for example, angioplasty and other interventional radiological procedures. Regardless of the type of procedure, any fluid injected into the patient must be sterile and contain a minimum of pyrogens.

A number of injector-actuated syringes and powered injectors for use in medical procedures such as angiography, computed tomography, ultrasound and NMR/MRI have been developed. U.S. Pat. No. 4,006,736, for example, discloses an injector and syringe for injecting fluid into the vascular system of a human being or an animal. Typically, such injectors comprise drive members such as pistons that connect to a syringe plunger. For example, U.S. Pat. No. 4,677,980, the disclosure of which is incorporated herein by reference, discloses an angiographic injector and syringe wherein the drive member of the injector can be connected to, or disconnected from, the syringe plunger at any point along the travel path of the plunger via a releasable mechanism. A front-loading syringe and injector system is also disclosed in U.S. Pat. No. 5,383,858, the disclosure of which is incorporated herein by reference.

As illustrated in FIG. 1, in several currently available injector systems (see, for example, U.S. Pat. No. 5,494,036 and Published U.S. Patent Application No. US 2004-0064041) an injector 10 includes two syringe interfaces 20a and 20b to which two syringes 50a and 50b are removably attachable. Injector 10 includes two drive members or pistons 30a and 30b which are operable to drive plungers 60a and 60b to pressurize fluid within the syringes so that two different fluids can be injected sequentially or simultaneously. For example, syringe 50a can contain a contrast medium and syringe 50b can contain a diluent or other medical fluid such as saline. As illustrated in FIG. 1, a T-connector 70 is typically provided to connect the fluid paths from each of syringes 50a and 50b to a fluid path connected to the patient. Check valves 80a and 80b can be provided to ensure that fluid cannot flow into either of syringe 50a and syringe 50b, respectively, via the fluid set attached to the syringes. As an alternative to a T-connector, a stopcock can be provided with check valves as described above. Unfortunately, these configurations add cost and only address parts of a needed device for these types of power injection systems. For example a check valve provides directional flow to prevent backflow however it does not provide the ability to perform a patency check. In a patency check, the plunger of one of the syringes in fluid connection with the patient is drawn rearward to check if blood is drawn into the fluid path. Drawing blood into the fluid path provides an indication that a catheter on the end of the patient fluid path is appropriately within a blood vessel.

It is desirable to develop improved devices, systems and method for use in connection with injector systems to reduce or eliminate the above and other problems associated with current injection systems while keeping cost of goods in check

SUMMARY OF THE INVENTION

In one aspect, the present invention provides a valve system for use in a system including a first source of a first pressurized fluid and a second source of a second pressurized fluid. The valve system includes a valve housing including a first inlet port adapted to be placed in fluid connection with the first source, a second inlet port adapted to be placed in fluid connection with the second source and an outlet port. The valve system further includes a backflow prevention system to prevent flow of the first pressurized fluid through the second inlet and to prevent flow of the second pressurized fluid through the first inlet port. The valve system is adapted to provide a fluid path between at least the first inlet port and the outlet port to enable fluid to be drawn from the outlet port to the first inlet port. Several of the valve systems of the present invention provide for flow from the first inlet port to the outlet port and concurrent flow from the second inlet port to the outlet port.

In several embodiments, the valve system can also include a bypass flow path to direct flow around the second check valve, thereby providing a fluid path between the outlet port and the second inlet port to enable fluid to be drawn from the outlet port to the second inlet port.

The backflow prevention system can, for example, include a first check valve in fluid connection with the first inlet port and a second check valve in fluid connection with the second inlet port. The valve system can further include a bypass flow path to direct flow around the first check valve, thereby providing the fluid path between the outlet port and the first inlet port to enable fluid to be drawn from the outlet port to the first inlet port.

The backflow prevention system can include a sealing member movable within the valve housing in response to pressure changes. The sealing member can have a normal state in which it is biased to block flow into the second inlet port, while a fluid path between the first inlet port and the outlet port is provided to enable fluid to be drawn from the outlet port to the first inlet port. The at least one sealing member can, for example, be biased by at least a first spring.

In one embodiment, the sealing member includes a piston member biased to abut a portion of the valve housing to block flow into the second inlet port. The piston has a passage therethrough in fluid connection with the outlet. The valve system can further include a valve housing member having a passage therethrough in fluid connection with the first inlet port. The first check valve in this embodiment can be in fluid connection with the passage in the valve housing member. The passage in the piston can be in fluid connection with the passage in the valve housing member. A fluid path can be provided around the housing member to provide the bypass flow path in fluid connection with the passage in the piston and the first inlet port when the piston is biased to abut the portion of the valve housing. Flow from the second fluid path can cause the piston to move out of abutment with the portion of the valve housing to provide a fluid connection between the second inlet port and the outlet port. The piston can be moved to abut the valve housing member to block the bypass flow path, while the passage in the piston remains in fluid connection with the passage in the valve housing member.

In several embodiments of the valve systems of the present invention, the backflow prevention system can include at least a first sealing member movable within the valve housing in response to pressure changes. The first sealing member can, for example, be biased to provide the fluid path between the first inlet port and the outlet port. The first sealing member can, for example, be biased by a first spring.

Flow from the second inlet port can cause movement of the first sealing member to block the fluid path between the first inlet port and the outlet port.

The valve system can also include a second sealing member moveable within the valve housing and a second spring positioned between the first sealing member and the second sealing member. Flow from the first inlet and concurrent flow from the second inlet causes the second spring to compress so that a fluid path is provided between the first inlet port and the outlet port and a fluid path is provided between the second inlet port and the outlet port.

In several other embodiment of the present invention, the backflow prevention system includes a deformable sealing member biased to block flow into the second inlet port. Flow of fluid into the second inlet port at a first pressure can, for example, deform a first portion of the sealing member to block flow into the first inlet port. Flow of fluid into the second inlet port at a second pressure higher than the first pressure can deform a second portion of the sealing member to open a fluid path between the second inlet port and the outlet port.

The valve housing can include a first housing member (for example, including the first inlet) and a second housing member (for example, including the second inlet port). The first housing member and the second housing member can be attached to form the valve housing, wherein the deformable sealing member is positioned between the first housing member and the second housing member. A fluid path can be provided between the first inlet port and the outlet port regardless of a state of the deformable sealing member. Flow into the first inlet port and concurrent flow into the second inlet port can cause flow from the first inlet port into the outlet port and concurrent flow from the second inlet port into the outlet port.

The backflow prevention system can also include a flexible conduit positioned within the valve housing to block the second inlet port from being in fluid connection with the outlet port. A passage through the conduit can provide the fluid path between the first inlet port and the outlet port to enable fluid to be drawn from the outlet port to the first inlet port. An increase in pressure in the second inlet port can result in compression of a first portion of the flexible conduit to close the fluid path between the first inlet port and the outlet port. A further increase in pressure in the second inlet port can cause a second portion of the flexible conduit to compress to create a fluid path between the second inlet port and the outlet port.

In another aspect, the present invention provides an injection system including: a first source of a first pressurized fluid; a second source of a second pressurized fluid, and a valve system as described above. In that regard, the valve system can include a valve housing including a first inlet port in fluid connection with the first source, a second inlet port in fluid connection with the second source and an outlet port. The valve system further includes a backflow prevention system to prevent flow of the first pressurized fluid through the second inlet and to prevent flow of the second pressurized fluid through the first inlet port. The valve system is adapted to provide a fluid path between at least the first inlet port and the outlet port to enable fluid to be drawn from the outlet port to the first inlet port. The first source can, for example, be a first syringe in fluid connection with a powered injector, and the second source can for example, be a second syringe in fluid connection with the powered injector.

In a further aspect, the present invention provides a valve system for use in a system including a first source of a first pressurized fluid and a second source of a second pressurized fluid. The valve system includes: a valve housing including a first inlet port adapted to be placed in fluid connection with the first source, a second inlet port adapted to be placed in fluid connection with the second source and an outlet port; at least one deformable sealing member in operative connection with the first inlet port and the second inlet port, the at least one deformable sealing member being biased to block flow into the second inlet port, and a fluid path between the first inlet port and the outlet port regardless of a state of the deformable sealing member. Flow of fluid into the second inlet port at a first pressure deforms a central portion of the sealing member to block flow into the first inlet port. Flow of fluid into the second inlet port at a second pressure, higher than the first pressure, deforms an outer portion of the sealing member to open a fluid path between the second inlet port and the outlet port. Flow into the first inlet port and concurrent flow into the second inlet port deforms the central portion of the deformable sealing member and causes flow from the first inlet port into the outlet port and concurrent flow from the second inlet port into the outlet port. In one embodiment, the valve housing includes a first housing member including the first inlet and a second housing member including the second inlet port. The first housing member and the second housing member can be attached to form the valve housing. The deformable sealing member is positioned between the first housing member and the second housing member. The outlet can, for example, be formed in one of the first housing member or the second housing member. The outlet port can also be formed upon attachment of the first housing member and the second housing member. In general, the housing can include two housing members that are attachable to form a housing including the first inlet, the second inlet port and the outlet port. Preferably, the at least one deformable sealing member is positionable between the housing members during assembly to provide for efficient and cost effective assembly.

The present invention also provide methods of delivering fluids using the above devices and systems.

In several embodiments, the present invention thus provides devices, systems and methods to provide input isolation to prevent backflow into fluid sources prior to coupling (that is, providing fluid connection between) one of the input ports of a valve system to the output port thereof. Moreover, the devices, systems and methods of the present invention provide also provide for checking for patency through at least one input ports of the valve system. In several embodiments, the devices, systems and methods of the present invention also provide for concurrent or dual flow through both of the input ports to the output port without user intervention.

The present invention, along with the attributes and attendant advantages thereof, will best be appreciated and understood in view of the following detailed description taken in conjunction with the accompanying drawings.

BRIEF DESCRIPTION OF THE DRAWINGS

FIG. 7A illustrates another embodiment of an injector system of the present invention including a dual shuttle valve system in which the shuttle or plug members are biased in a normal position to provide fluid connection between a second source of fluid and an outlet port, while closing fluid connection between the first source of fluid and the outlet port.

FIG. 7B illustrates the dual shuttle valve of FIG. 7A wherein the plug members are in a position to close the fluid path between the second fluid source and the outlet port and close the fluid path between the first fluid source and the outlet port.

FIG. 7C illustrates the dual shuttle valve of FIG. 7A wherein the plug members are in a position to close the fluid path between the second fluid source and the outlet port and open the fluid path between the first fluid source and the outlet port.

FIG. 7D illustrates the dual shuttle valve of FIG. 7A wherein the plug members are in a position to open the fluid path between the second fluid source and the outlet port and open the fluid path between the first fluid source and the outlet port, thereby allowing simultaneous flow from the first fluid source and the second fluid source to the outlet port.

FIG. 8A illustrates another embodiment of an injector system of the present invention including a valve system to control fluid connections between two sources of fluid and an outlet port.

FIG. 8B illustrates valve system of FIG. 8A in a state to prevent fluid flow from either source of fluid.

FIG. 8C illustrates the valve system of FIG. 8A in a state permitting flow from the first fluid source to the outlet port, while preventing fluid flow from the second fluid source to the outlet port.

FIG. 8D illustrates the valve system of FIG. 8A in a state permitting simultaneous flow and mixing from both fluid sources.

FIG. 9A illustrates another embodiment of a valve system of the present invention.

FIG. 9B illustrates the valve system of FIG. 9A in a state permitting flow from a first inlet port to an outlet port while preventing flow from a second inlet port to the outlet port.

FIG. 9C illustrates the valve system of FIG. 9A wherein pressure from the second inlet port closes the fluid path between the first inlet port and the outlet port.

FIG. 9D illustrates the valve system of FIG. 9A in a state permitting flow from the second inlet port.

FIG. 9E illustrates a side view of the flexible diaphragm of the valve system of FIG. 9A.

FIG. 10A illustrates an embodiment of a valve system of the present invention in a normal state providing fluid connection between a first inlet port and an outlet port.

FIG. 10B illustrates the valve system of FIG. 10A in a state preventing flow from either the first or second inlet port to the outlet port.

FIG. 10C illustrates the valve system of FIG. 10A in a state permitting flow from the second inlet port to the outlet port.

FIG. 10D illustrates the valve system of FIG. 10A in a state permitting simultaneous flow and mixing from both inlet ports.

DETAILED DESCRIPTION OF THE INVENTION

Figure 1:
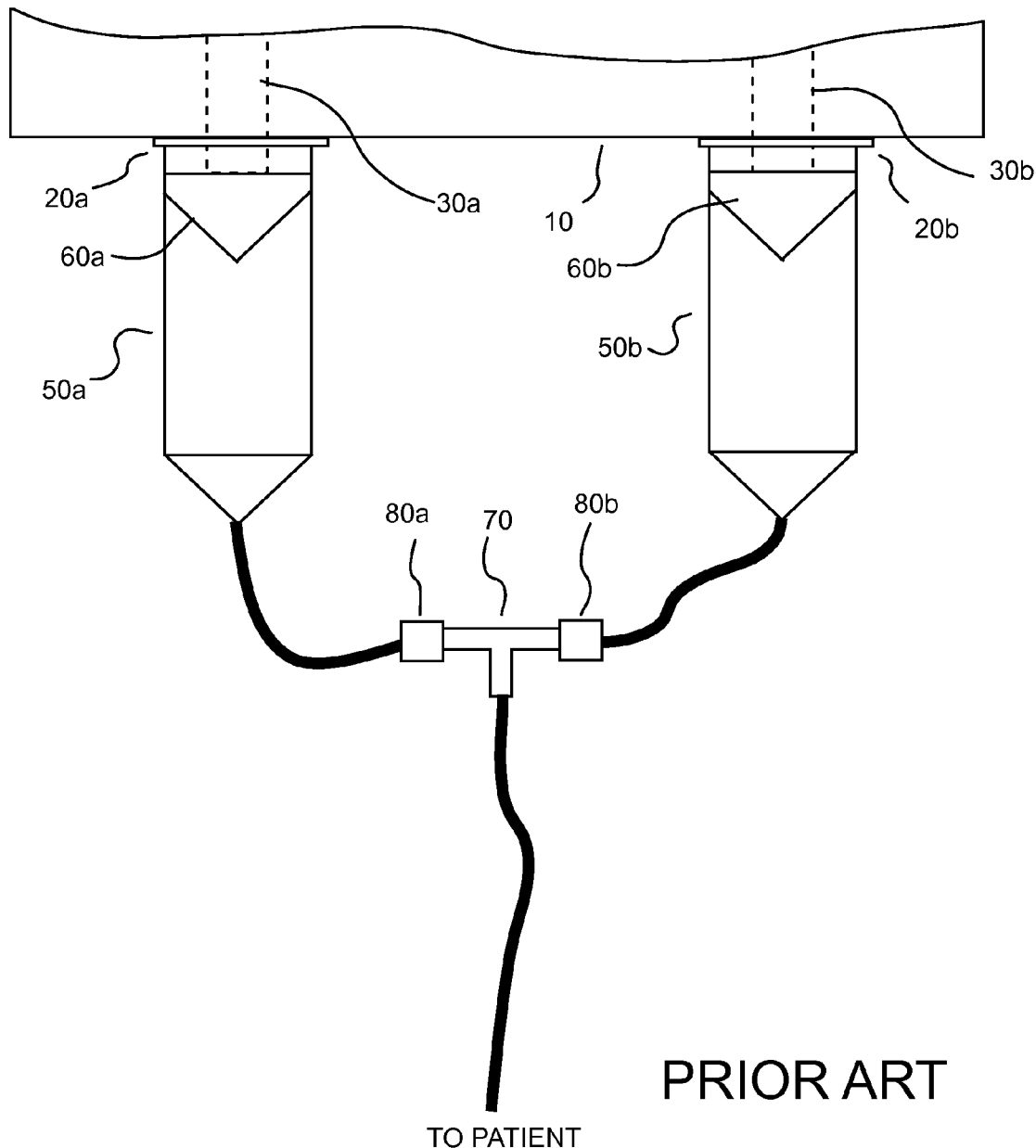
FIG. 1 is a schematic illustration of a currently available injector system including two syringes in which the outflow of each syringe is connected to a patient fluid path via a T-connector, and wherein check valves are provided to prevent backflow into the syringes.
Figure 2A:
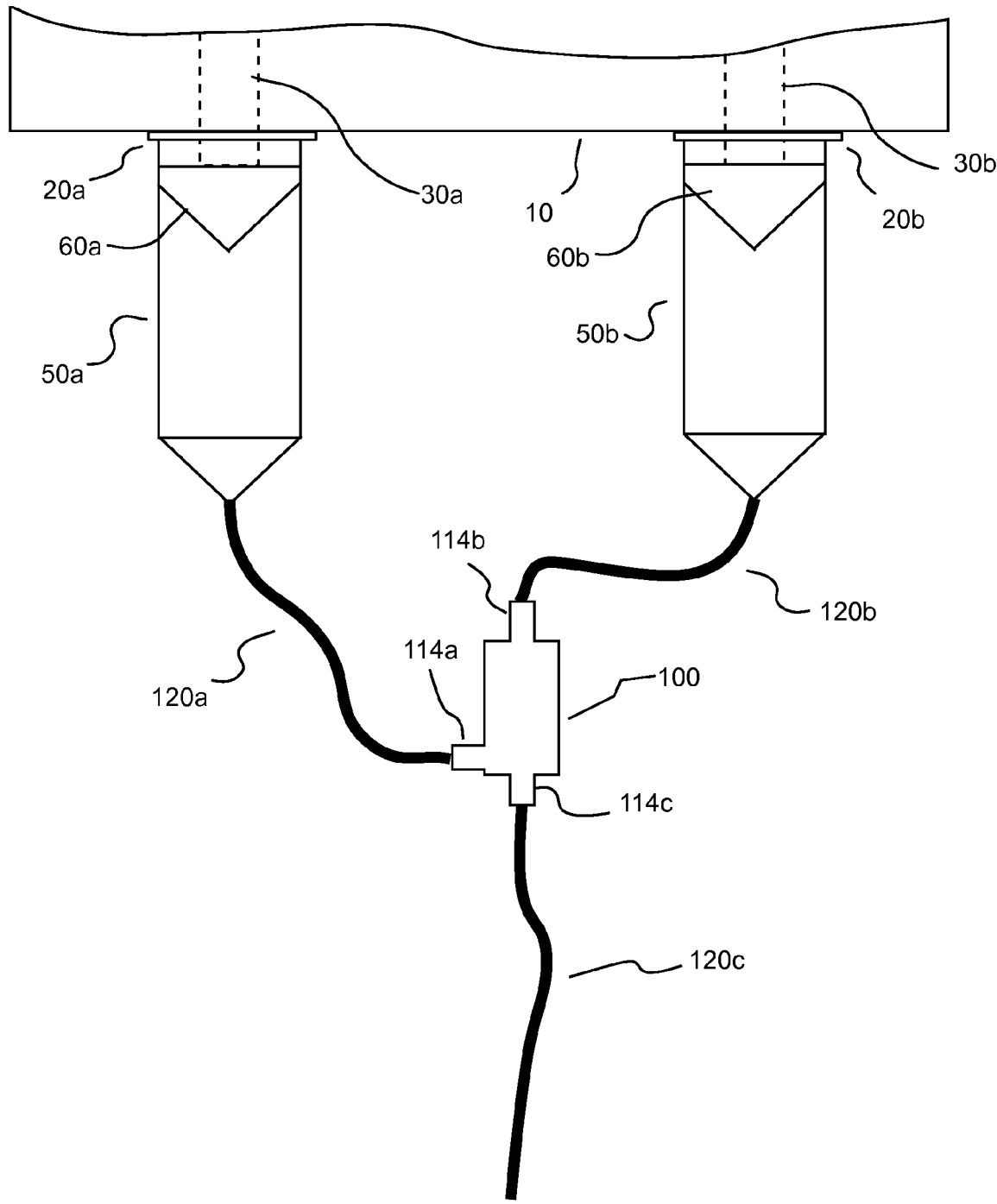
FIG. 2A illustrates an embodiment of an injector system of the present invention including an embodiment of a valve system of the present invention.

FIG. 2A illustrates an embodiment of an injector system of the present invention in which an injector 10 includes two syringe interfaces 20a and 20b to which two syringes 50a and 50b are attachable. As discussed in connection with FIG. 1, injector 10 includes two drive members or injector pistons 30a and 30b which are operable to drive plungers 60a and 60b to pressurize fluid within syringes 50a and 50b, respectively, so that two different fluids can be injected sequentially or simultaneously. For example, syringe 50a can contain a contrast medium and syringe 50b can contain a diluent such as saline or another medical fluid. As also illustrated in FIG. 2A, an automatic dual flow, anti-mixing valve system 100 is provided to connect fluid paths 120a from each of syringes 50a and 50b, respectively, to a fluid path 120c connected to the patient.

As illustrated in FIGS. 2B through 2E, valve 100 includes a first valve body 106 and second valve body 108 which can, for example, be permanently attached to form a valve housing 110. Valve housing 110 includes two inlet ports 114a and 114b and an outlet port 114c. Inlet port 114a is connected to fluid path 120a (for example, flexible tubing) which provides for fluid connection between syringe 50a and valve 100. Similarly, inlet port 114b is connected to fluid path 120b (for example, flexible tubing) which provides for fluid connection between syringe 50b and valve 100 and allows fluid from syringe 50b to flow axially through a bore or passage 140a in a valve piston 140 to outlet port 114c. Valve piston 140 is able to move axially within valve housing 110. Valve piston 140 is normally biased upward (for example, via a spring 122a) against the top (in the orientation of FIG. 2B) inside surface of valve housing 110. In the normal position or state, an annular clearance 144, which is in fluid connection, with inlet port 114a is blocked from fluid connection with outlet port 114c by the contact of valve piston 140 with the interior surface of housing 110. Fluid pressure from inlet port 114a applies force on an angled top surface 144 of the valve piston 140, and causes the valve piston 140 to move downward, compressing spring 122a and providing for fluid connection between inlet port 114a and outlet port 114c (see FIG. 2E).

Valve 100 has four distinct operating modes. In a first mode, only fluid from syringe 50b (for example, saline) can be injected. In this operating mode, flow from syringe 50a is prevented. As described above, spring 122a normally maintains the valve piston 140 in the extended (raised) or normal position as illustrated in FIG. 1A. As the injector's piston 30b is extended, fluid is forced to flow from syringe 50b, through fluid path 120b and into bore 140 (via inlet 114b). Fluid from syringe 50b can flow thorough a first one-way check valve 130 in fluid connection with bore 140a and on to the patient. It is also possible for fluid from syringe 50b to flow through an annular space 156 between valve housing 110 and housing member 152 and through a space 154 between housing member 152 and piston 144, to enter center bore 140a of the valve piston 140 and on to the patient. Flow will normally occur through both of these fluid paths in parallel. Because both fluid pressure and the return spring 122a keep the valve piston 140 in its extended (raised) position, it is not possible for the fluid from syringe 50b to flow into syringe 50a. A second check valve 132 further precludes flow from the syringe 50b into syringe 50a.

In a second mode, only fluid form syringe 50a can be injected. Fluid flows from syringe 50b into inlet 114a via fluid path 120a and passes through second one-way check valve 132. The pressure of fluid from syringe 50a applies force to top surface 144 of valve piston 140, forcing valve piston 140 downward until the lower surface (in the orientation of FIGS. 2B and 2E) of the valve piston 140 abuts against housing member 152 (see FIG. 2E). Return spring 122a is compressed as valve piston 140 is forced downward. As valve piston 140 moves downward, a fluid connection is formed between outlet port 114c and annular clearance or volume 148. This fluid connection allows contrast to flow from inlet port 114a to outlet port 114c and therethrough to fluid path 120c and to the patient. Check valve 130 prevents fluid from flowing from the syringe 50a into syringe 50b via bore 140a.

In a third mode of operation, fluid from both syringe 50a and syringe 50b can be simultaneously injected. Fluid flows from syringe 50a and passes through volume 148 and outlet port 114c as described above. As also described above, fluid flows from syringe 50b and passes through check valve 130, through center bore 140a of valve piston 140, and on to the patient. It is possible, and desirable, for fluids from syringe 50a and 50b (for example, contrast and saline) to mix together in, for example, annular clearance or volume 148. Check valve 130 prevents saline from flowing into syringe 50b, and check valve 13e prevents contrast from flowing into syringe 50a.

Figures 2B, 2C:
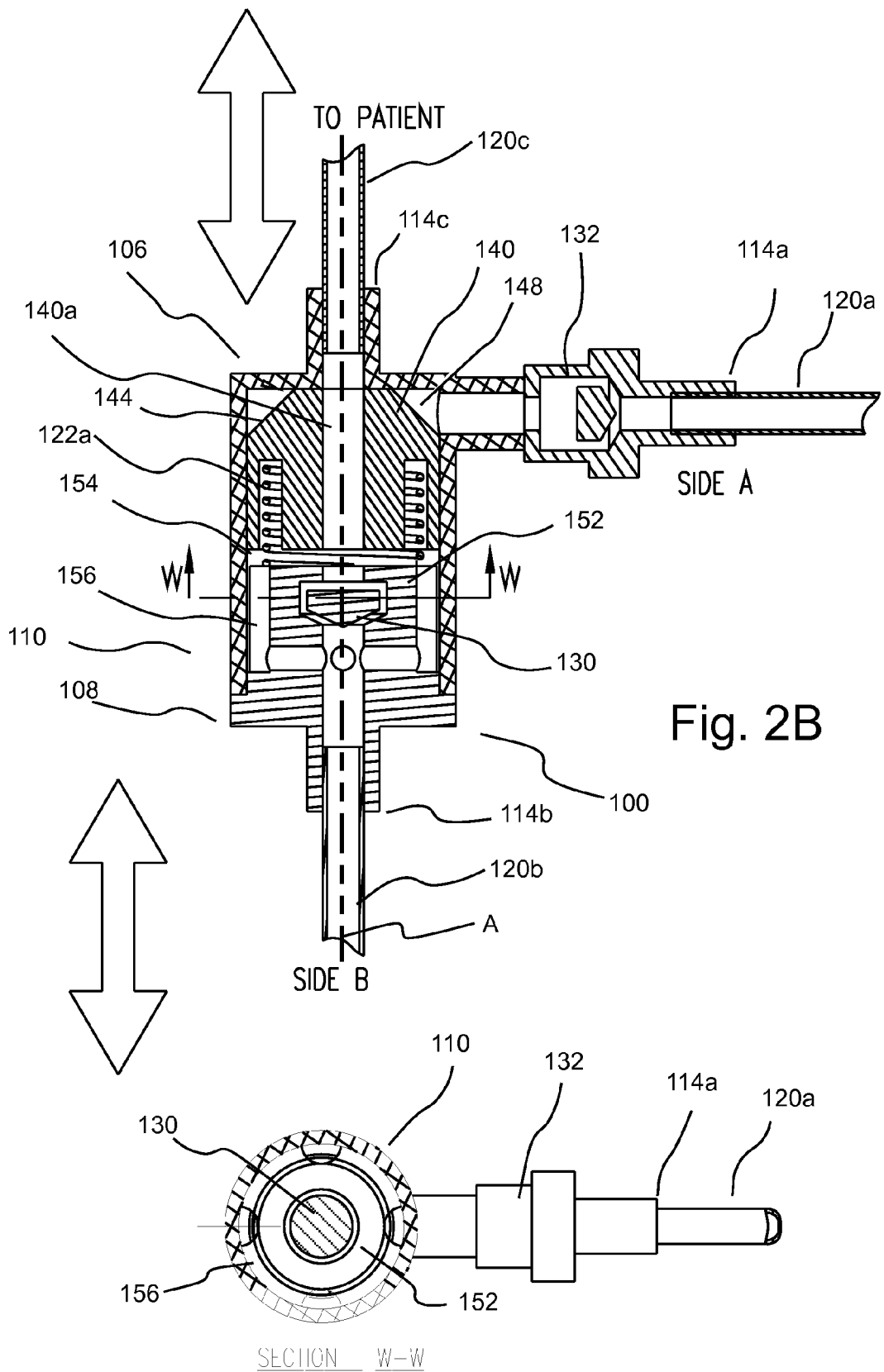
FIG. 2B illustrates a cross-sectional view of the valve system of FIG. 2A.
FIG. 2C illustrates another cross-sectional view of the valve system of FIG. 2B.
Figure 2D:
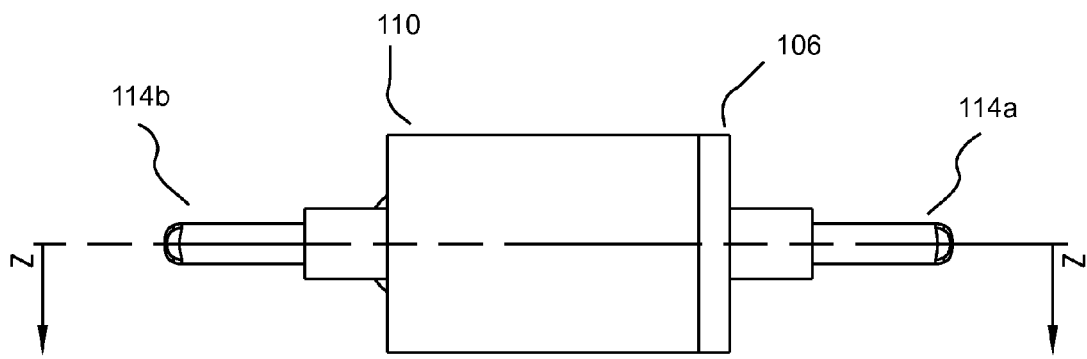
FIG. 2D illustrates a side view of the valve system of FIG. 2B.
Figure 2E:
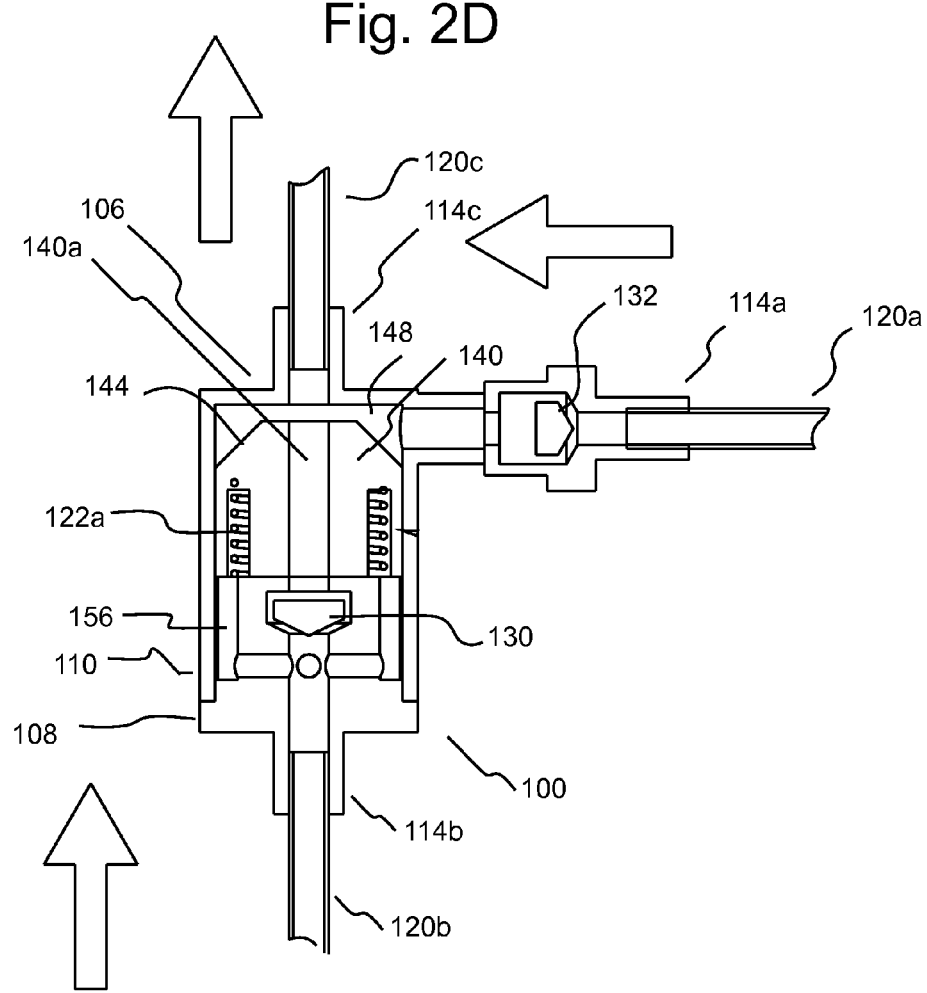
FIG. 2E illustrates a cutaway view of the valve system of FIG. 2B.

In a fourth mode of operation, a patency check can be performed. As there is no flow from syringe 50a, return spring 122a maintains valve piston 140 in the extended (raised) position as illustrated in FIG. 2B during the entire patency check process. Annular space or volume 152 is in fluid connection with center bore 140a of the valve piston 140 (and therethrough with outlet 114c and the patient) in this valve state. In this state, retraction of injector piston 30b (and, thereby, retraction of plunger 60b of syringe 50b) causes fluid to be drawn from the patient (via the fluid connection between center bore 140a, annular space 152 and inlet port 114b, which provides a bypass around/of check valve 130).

Figure 3A:
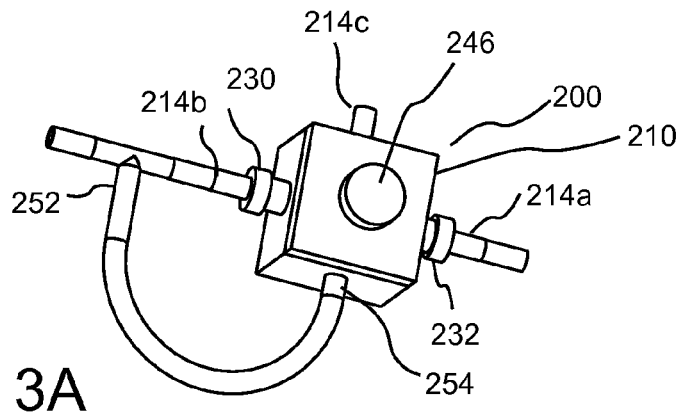
FIG. 3A illustrates a perspective view of another embodiment of a valve system of the present invention for use in connection with an injector system as, for example, illustrated in FIG. 2A.
Figure 3B:
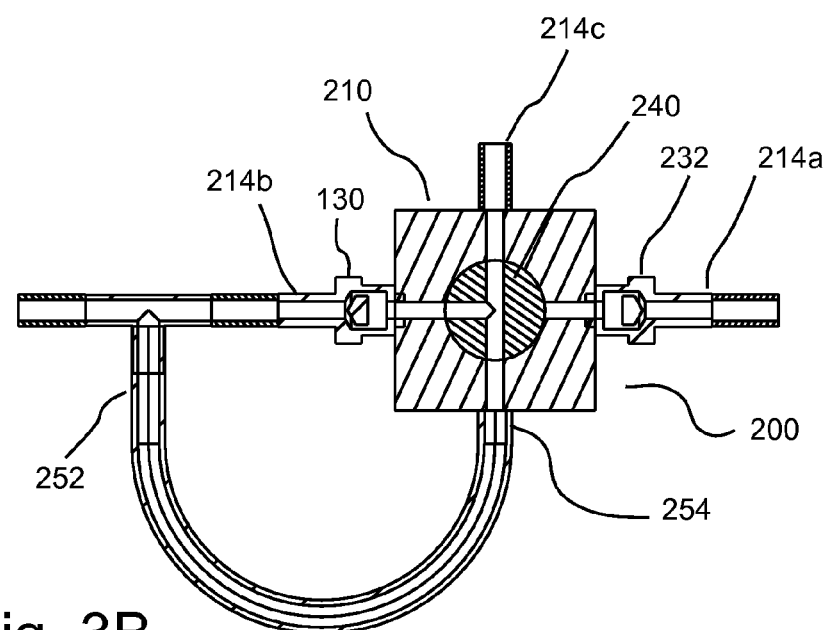
FIG. 3B illustrates a cross-sectional view of the valve system of FIG. 3A wherein an integral three-way stopcock valve is set to open a fluid path between a source of a first fluid and an outlet of the valve system.
Figure 3C:
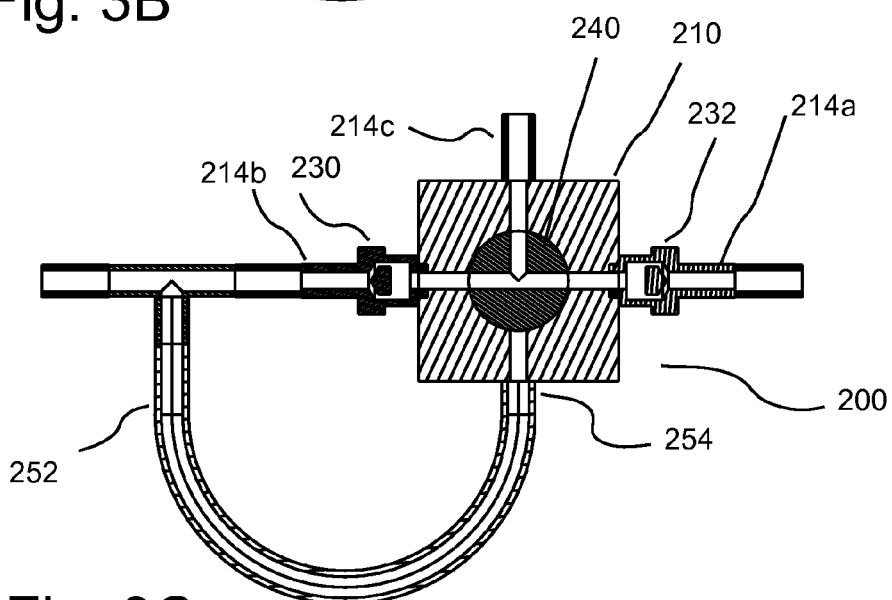
FIG. 3C illustrates a cross-sectional view of the valve system of FIG. 3A wherein an integral three-way stopcock valve is set to open a fluid path between the source of the first fluid and a source of a second fluid and the outlet of the valve system.

FIGS. 3A-3C illustrate another embodiment of a valve system 200 of the present invention. Valve 200 includes a housing 210, which includes a first inlet port 214a that can, for example, be placed in fluid connection with syringe 50a via, for example, fluid path 120a. A second inlet port 214b of housing 210 can, for example, be placed in fluid connection with syringe 50b via, for example, fluid path 120b. Housing 210 also includes an outlet port 214c which can be placed in fluid connection with a patient via, for example, fluid path 120c. A bypass fluid path 252 is in fluid connection between inlet port 214b and a bypass port 254 of housing 210.

Rotatably disposed within housing 210 is a three-way stop cock valve member 240 (see FIGS. 3B and 3C). A connector 246 (see FIG. 3A) is provided to effect either manual control or automated control (for example, via servos or other actuators as known in the art) of the state or position of valve member 240 and, thereby, the state of valve system 200. A first state of valve system 200 is illustrated in FIG. 3B in which inlet port 214b and bypass port 254 are place in fluid connection with outlet port 214c. In this state, fluid can be injected into the patient via, for example, syringe 50b or other pressurizing device in fluid connection with inlet port 214b. As no fluid connection is provided between inlet port 214b and inlet port 214a in this state, no fluid can enter, for example, syringe 50a in fluid connection with inlet port 124a. Further, a patency check can be performed in the valve state of FIG. 3A by, for example, retracting plunger 60b of syringe 50b in fluid connection with inlet port 214b.

In another valve state illustrated in FIG. 3C, fluid connection is provided between each of inlet port 214a and inlet port 214b and outlet port 214c. Fluid can thus be injected into the patient via either inlet port 214a or inlet port 214b. One-way check valve 230 prevents fluid from exiting valve system 200 via inlet port 214b, while one-way check valve 232 prevents fluid from exiting valve system 200 via inlet port 214a (thereby preventing backmixing in, for example, syringes 50a and 50*b*). Simultaneous flow of fluid to the patient from both inlet ports 214*a* and 214*b* can also be effected in the valve state of FIG. 3C.

Figure 4A:
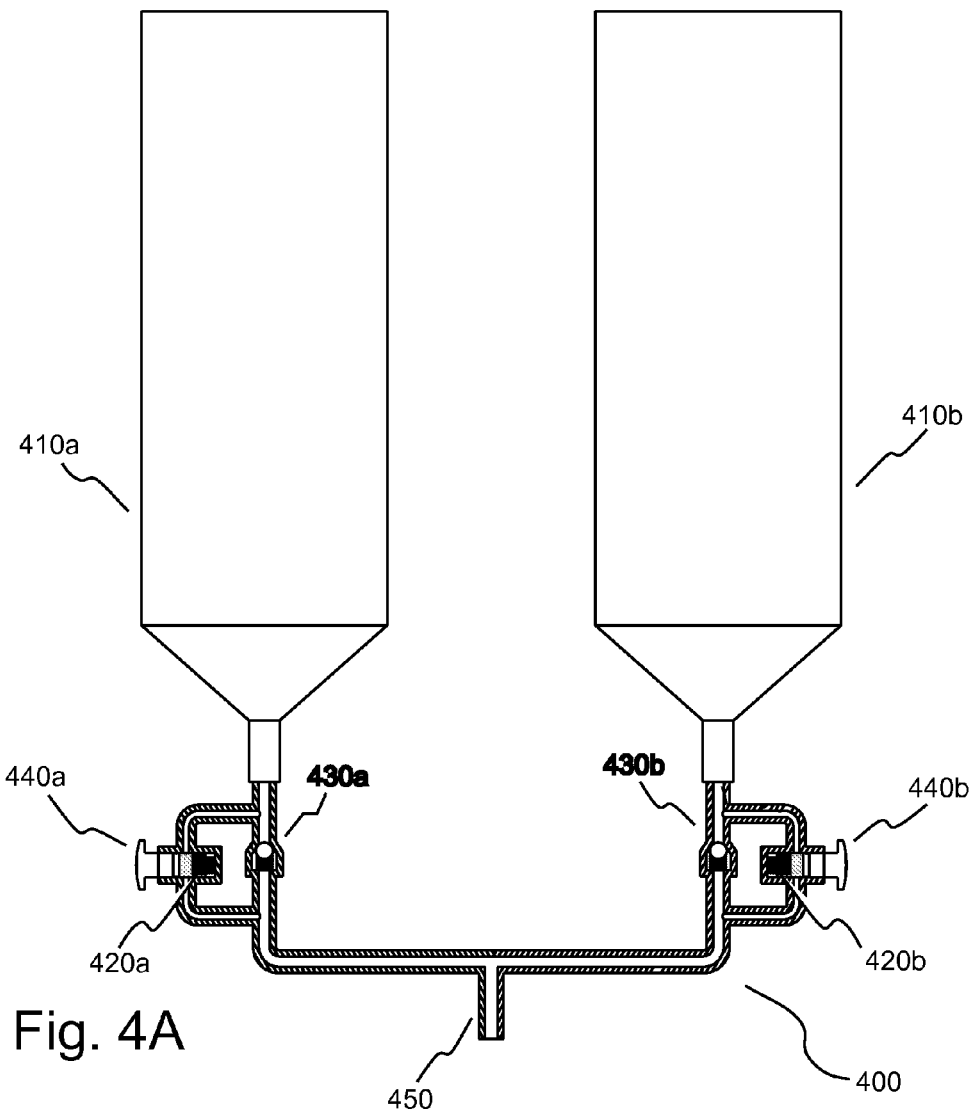
FIG. 4A illustrates another embodiment of an injector system of the present invention including valve systems which permit flow without the reverse mixing.
Figure 4B:
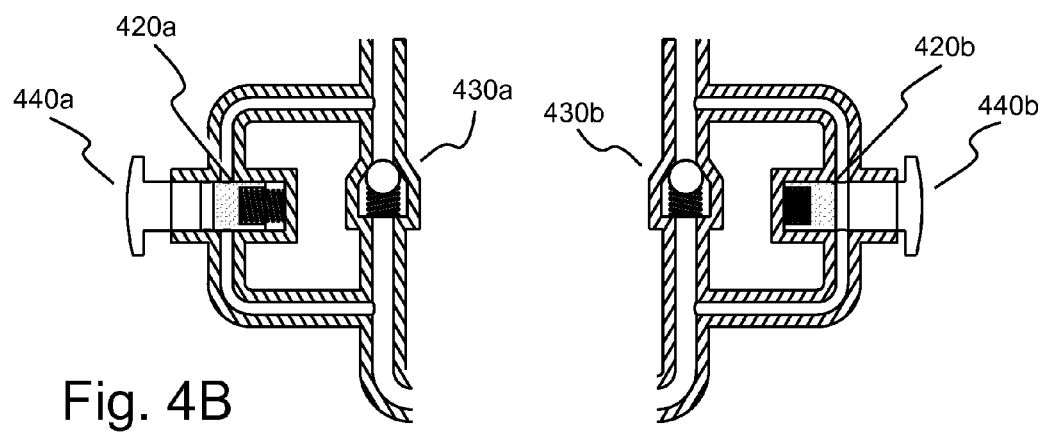
FIG. 4B illustrates an enlarged cross-sectional view of the valve systems of the injector system of FIG. 4A.

In another embodiment of an injection system of the present invention as illustrated in FIGS. 4A and 4B, a valve system 400 includes first and second actuatable (for example, push-button) valves 420*a* and 420*b* which allow an operator (either manually or automatically) to access fluids from either or both of reservoirs 410*a* and 410*b* (for example, syringes). One way check valves 430*a* and 430*b* prevent reverse mixing or backflow of fluids into reservoirs 410*a* and 410*b*. First reservoir 410*a* can, for example, be a container or syringe for contrast fluids, while second reservoir 410*b* can be a container or syringe for saline. First and second actuatable valves 420*a* and 420*b* are normally in a closed position. Examples of such valves are known in the valve arts as trumpet valves. First and second actuators or push buttons 440*a* and 440*b* are manually or automatically activatable by an operator to open first or second valves 420*a* and 420*b*, to open a fluid path between reservoir 400*a* or 400*b*, respectively, and outlet 450 to provide for a patency check or to provide for refilling. Check valves 430*a* and 430*b* allow fluid to flow from reservoir 410*a* and/or 410*b*, but prevent flow into reservoirs 410*a* and 410*b*, respectively. A common outlet port 450 delivers fluid from either or both of first and second reservoirs 410*a* and 410*b* to the patient.

If first reservoir 410*a* is pressurized, check valve 430*a* opens and allows fluid flow to outlet port 450. However, fluid cannot flow backwards through check valve 430*b* into second reservoir 410*b*. If second reservoir 410*b* is pressurized, check valve 430*b* opens and allows flow to outlet port 450. However, fluid cannot flow backwards through first check valve 430*a* into first reservoir 410*a*. If both reservoirs 410*a* and 410*b* are pressurized, check valves 430*a* and 430*b* open and allow the fluids to flow to outlet port 450. Mixing can only take place downstream of check valves 430*a* and 430*b*.

FIG. 4B provides an enlarged view of valves 420*a* and 420*b* showing second valve 420*b* opened by actuation of button 440*b*, while first valve 420*a* is in a closed state. First and second actuatable valves 420*a* and 420*b* are provided so that an operator can selectively bypass first and second check valves 430*a* or 430*b* so fluid can be moved in either direction through these valves. This can be done to perform a patency check or to refill reservoirs 410*a* and 410*b*.

Figure 5A:
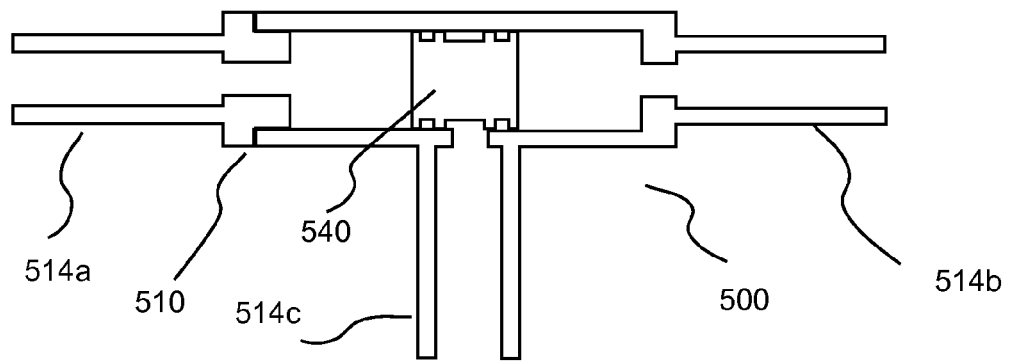
FIG. 5A illustrates another embodiment of a valve system of the present invention wherein a plug member is slidably disposed within the valve housing.
Figure 5B:
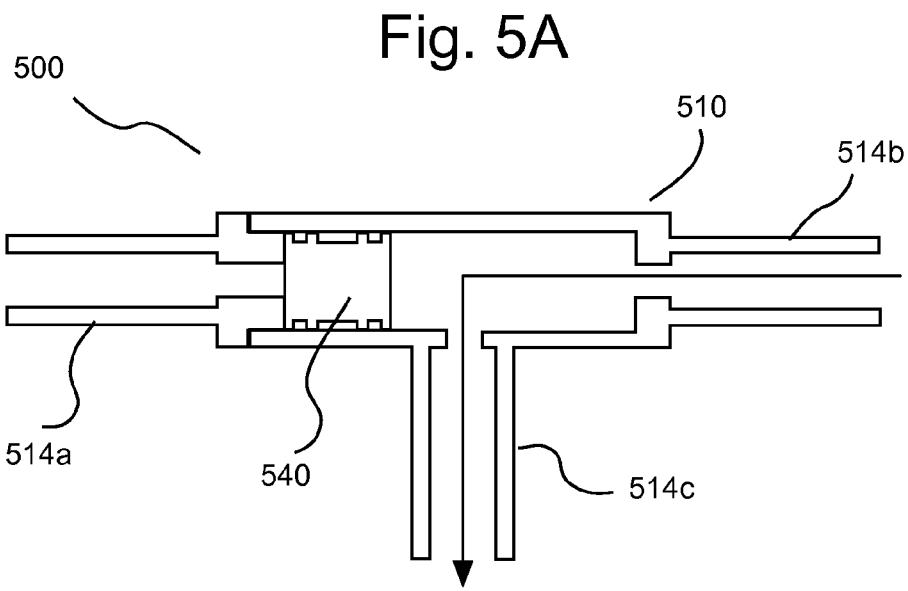
FIG. 5B illustrates the valve system of FIG. 5A wherein the plug member is positioned to provide fluid connection between a first fluid source and an outlet port and to block fluid connection between a second fluid source and the outlet port.
Figure 5C:
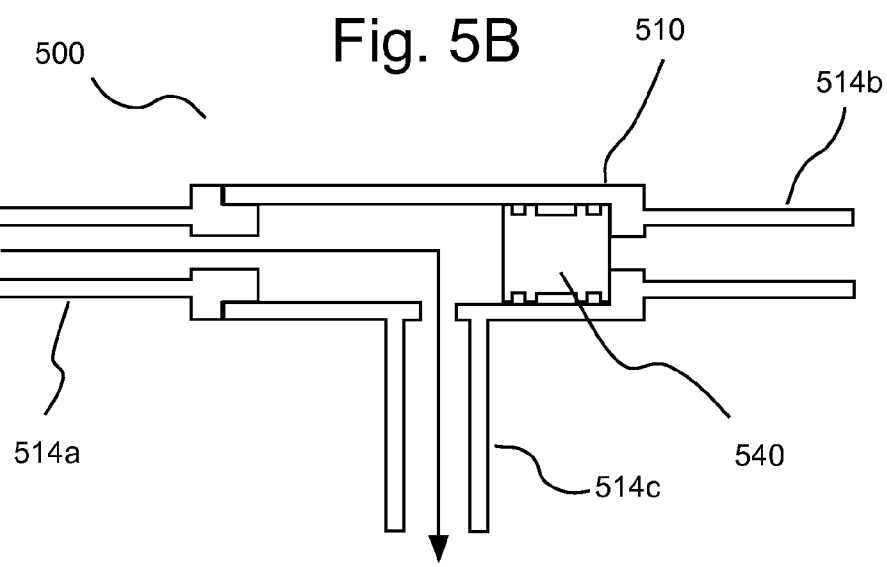
FIG. 5C illustrates the valve system of FIG. 5A in which the plug member is positioned to provide fluid connection between the second fluid source and the outlet port and to block fluid connection between the first fluid source and the outlet port.

FIGS. 5A-5C illustrate another embodiment of a valve 500 of the present invention including a housing 510 in which a moveable plug, shuttle or sealing member 540 is slidably disposed. Housing 510 includes a first inlet port 514*a*, a second inlet port 514*b* and an outlet port 514*c*. In FIG. 5A, plug member 540 is illustrated in an arbitrary or neutral starting position. In FIG. 5B, pressurized fluid from, for example, a syringe in fluid connection with second inlet port 514*b* causes plug member to slide to the left or toward first inlet port 514*a* so that second inlet port 514*b* is placed in fluid connection with outlet port 514*c*. Plug member 540 blocks first inlet port 514*a* from fluid connection with second inlet port 514*b* and outlet 514*c*, preventing flow of fluid from second inlet port 514*b* into first inlet port 514*a*. In the position or state illustrated in FIG. 5B, fluid can flow to (for example, for a patency check) or from inlet port 514B. In FIG. 5C, pressurized fluid from, for example, a syringe in fluid connection with first inlet port 514*a* causes plug member 540 to slide to the right or toward second inlet port 514*b* so that first inlet port 514*a* is placed in fluid connection with outlet port 514*c*. Plug member 540 blocks second inlet port 514*b* from fluid connection with first inlet port 514*a* and outlet 514*c*, preventing flow of fluid from first inlet port 514*a* into inlet second port 514*b*. In the position or state illustrated in FIG. 5C, fluid can flow to or from inlet port 514*c*.

Figure 6A:
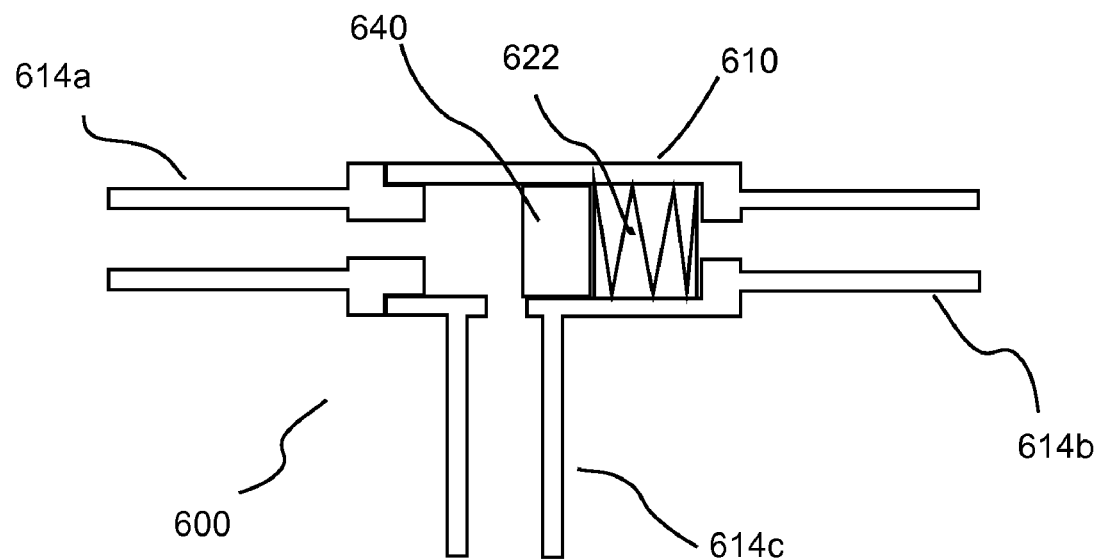
FIG. 6A illustrates another embodiment of a valve system of the present invention in which the plug member is biased in a position to provide fluid connection between a first fluid source and an outlet port while preventing fluid connection between a second fluid source and the outlet port.
Figure 6B:
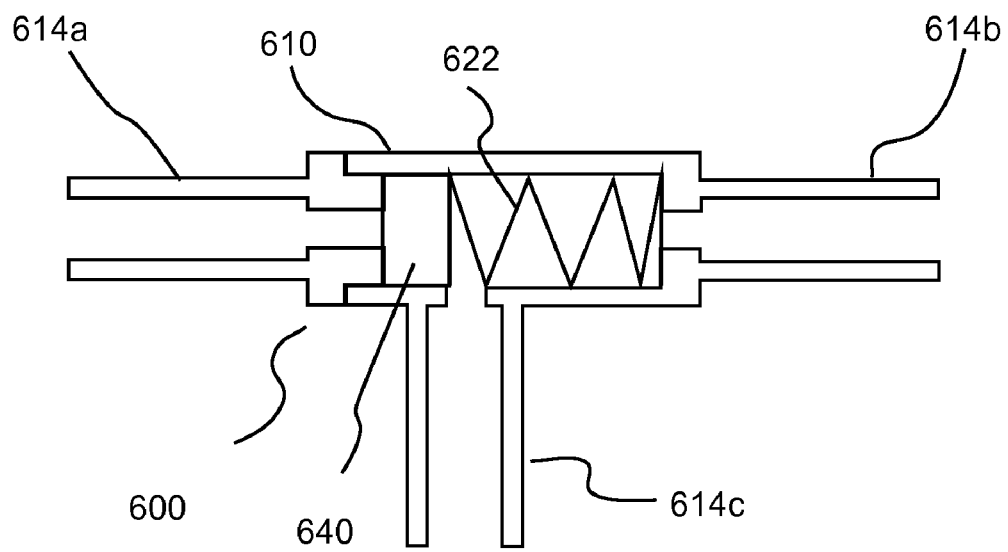
FIG. 6B illustrates the valve system of FIG. 6A in which pressurized flow from the second fluid source moves the plug member to a position to provide fluid connection between the second fluid source and the outlet port while preventing fluid connection between the first fluid source and the outlet port.

FIGS. 6A and 6B illustrate another embodiment of a valve 600 of the present invention which includes a valve housing 610. Valve housing includes a first inlet port 614*a*, a second inlet port 614*b* and an outlet port 614*c*. A plug, shuttle or sealing member 640 is slidably positioned within housing 610. In this embodiment plug member, is biased (for example, via spring 622) in the state or position illustrated in FIG. 6A in which first inlet port 614*a* is in fluid connection with outlet port 614*c*. In this position, second fluid port 614*b* is blocked from fluid connection with first inlet port 614*a* and with outlet port 614*c*. In the state of FIG. 6A pressurized fluid entering first inlet port 614*a* can flow out of outlet port 614*c* to a patient, while flow of fluid from first inlet port 614*a* through second inlet port 614*b* is prevented. Also in this state, a patency check can be performed via, for example, a syringe in fluid connection with first inlet port 614*a*. In FIG. 6B, pressurized fluid entering valve 600 via second inlet port 614*b* overcomes the force of spring 622, causing plug member 640 to move toward first inlet port 614*a*. Fluid connection between first fluid port 614*a* and either outlet port 614*c* or second inlet port 614*b* is blocked before any fluid from second inlet port 614*b* can exit outlet port 614*c*.

FIG. 7A illustrates an embodiment of an injection system of the present invention including a dual shuttle valve 700 to control flow from two fluid sources or reservoirs 710*a* and 710*b*. Valve 700 allows reverse flow to one reservoir to, for example, provide for a patency check, but prevents mixing between reservoirs 710*a* and 710*b*. Valve 700 further allows flow from either or both of reservoirs 710*a* and 710*b* as desired. The valve body or housing 720 includes a first inlet port 724*a*, a second inlet port 724*b* and an outlet port 724*c*. Valve housing 720 further includes a first plug, shuttle or sealing member 730*a* moveably/slidably disposed therein and a second plug, shuttle or sealing member 730*b* moveably/slidably disposed therein. A first biasing spring 740*a* is positioned between first plug member 730*a* and second plug member 730*b*, and a second biasing spring 740*b* is disposed between second plug member 730*b* and a second inlet side of valve housing 720.

First plug member 730*a* is slideable in valve housing 720 to control flow between first reservoir 710*a* and outlet port 724*c*. Second plug member 730*b* is slideable in valve body 720 to control flow from second reservoir 710*b* to outlet port 724*c*. First biasing spring 740*a* primarily positions first shuttle 730*a* inside valve body 720. Second biasing spring controls the position of both first and second plug member 730*a* and 730*b*. Outlet port 724*c* delivers fluid from first and/or second fluid reservoir 710*a* and 710*b* to a patient under treatment.

In FIG. 7A, valve housing 720 is illustrated in the "normal" position or state. In this state, reservoir 710*a* is shut off from delivering fluid as first biasing spring 740*a* has biased first plug member 730*a* into a position blocking the fluid path to outlet port 724*c*. However, reservoir 710*b* is allowed to deliver fluid to outlet port 724*c* as second plug member 730*b* is biased by the second biasing spring 740*b* so that second reservoir 710*b* is in fluid connection with outlet 750. In this normal position, fluid can flow in either direction through valve body 720 (that is, from inlet port 724*b* to outlet port 724*c* or in reverse, providing, for example, for fluid delivery from second reservoir 710*b*, filling of second reservoir 710*b* or a patency check).

In FIG. 7B, fluid in first reservoir 710*a* is pressurized. As the pressure from reservoir 710*a* increases, force on first plug member 730*a* causes first biasing spring 740*a* to compress slightly, which pushes second plug member 730*b* toward second inlet port 724b and, in turn, compresses second biasing spring 740b. As this occurs, second plug member 730b closes the fluid path from reservoir 710b to outlet port 724c before the fluid path between first reservoir 710a and outlet port 724c is opened.

As illustrated in FIG. 7C, as the pressure in reservoir 710a increases further, first biasing spring 740a is further compressed more by the force upon first plug member 730a, opening the fluid path between first reservoir 710a and outlet port 724c and allowing the fluid in first reservoir 710a to flow to outlet port 724c. However, the fluid path between reservoir 710b and outlet port 724c remains closed.

In FIG. 7D, the pressure in reservoir 710b is increased while flow is maintained from reservoir 710a. Second plug member 730b is forced in the direction of first inlet port 724a, compressing first biasing spring 740a. Second biasing spring 740b is expanded to approximately its normal position, opening the fluid path between second reservoir 710b and outlet port 724c and allowing flow from second reservoir 710b to outlet port 724c. In the state illustrated in FIG. 7D, simultaneous flow and mixing occurs downstream, but backflow into and mixing within reservoirs 710a and 710b is prevented.

FIG. 8A illustrates an embodiment of a fluid delivery or injection system of the present invention including a spool and check valve system 800 to connect two fluid reservoirs 810a and 810b (via, first inlet port 824a and second inlet port 824b, respectively) to a common outlet port 824c. A spool valve assembly 830 is slideable within valve housing 820, and forms a sealing engagement with valve housing 820 on the outside diameter of spool valve assembly 830. In the normal position or state as illustrated in FIG. 8A, the fluid path between second reservoir 810b and outlet port 824c is in an open state to allow fluid to flow from second reservoir 810b to outlet port 824c. A spring 840 biases spool valve assembly 830 into a position providing fluid connection between second reservoir 810b and outlet port 824c, thereby providing for flow from first reservoir 820b and reverse flow to first reservoir 820b (for example, for filling or for a patency check). The fluid path between second reservoir 810a and outlet port 824c is closed off by a spool or plug member 832 in spool valve assembly 830.

FIG. 8B illustrates that a pressure increase in reservoir 810a (while reservoir 810b remains unpressurized) forces spool valve assembly 830 toward second inlet port 824b and collapses spring 840 slightly. In this position, the fluid path between first inlet port 824a and outlet port 824c is closed, while the fluid path between second fluid inlet port 824b and outlet port 824c remains closed, and fluid cannot flow from either reservoir 810a or 810b to outlet port 824c.

As illustrated in FIG. 8C, as the pressure is increased within first reservoir 810a, spool valve assembly 830 is forced further toward second inlet port 824c, further collapsing spring 840, and opening the fluid path between first inlet port 824a and outlet port 824c, thereby connecting fluid reservoir 810a with outlet port 824c. In the state illustrated in FIG. 8C, the fluid path between second inlet port 824b and outlet port 824c is closed by spool valve assembly 830 and fluid flow from reservoir 810b remains blocked, thus preventing any mixing of the fluids from the reservoirs. A one-way check valve 850 further prevents flow from fluid reservoir 810a into reservoir 810b.

In FIG. 8D, both reservoirs 810a and 810b are pressurized. Fluid from reservoir 810a flows through valve housing 820 and spool valve assembly 830 to outlet port 824c. Fluid from reservoir 810b forces one-way check valve 850 (for example, a ball check valve as known in the art) to open, allowing fluid to flow to the outlet port 824c. The state illustrated in FIG. 8D permits the simultaneous flow of fluids from both reservoirs 810 and 810b. If flow stops from one of reservoirs 810a or 810b, spool valve assembly 830 or check valve 850 operate as described above to automatically prevent any mixing between reservoirs 810a and 810b.

FIGS. 9A-9F illustrate another embodiment of a valve system 900 of the present invention. In the illustrated embodiment, valve 900 includes a first or right (in the orientation of FIGS. 9A through 9D) valve housing 910a and a second or left valve housing 910b, which can, for example, be permanently connected. A flexible diaphragm 920 controls flow through valve system 900 in response to pressure from a first fluid (for example, saline) entering a first inlet port 930 or a second fluid (for example, a contrast medium) entering a second inlet port 940. Fluid exits valve system 900 via an exit port 970.

Figure 9G:
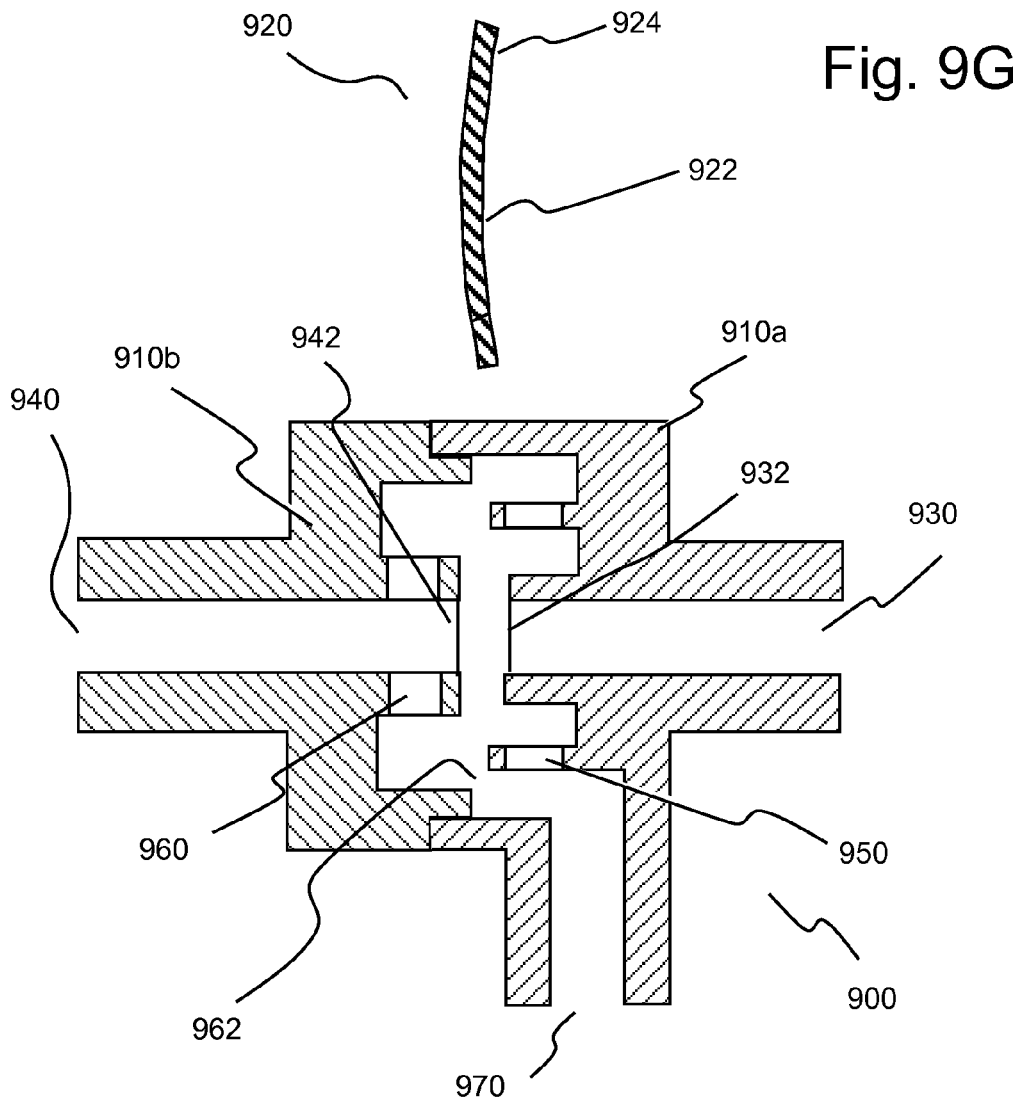
FIG. 9G illustrates the valve system of FIG. 9A in a disassembled state.

FIGS. 9A and 9B illustrate valve system 900 in its normal state. In this state, fluid can flow from a source of fluid in connection with first inlet port 930 (for example, a syringe in fluid connection with first fluid path 980a), passing through an exit end 932 of inlet port 930 and through a passage 950 to outlet port 970 (see FIG. 9B). It is also possible to perform a patency check via second inlet port 940 in the normal state.

In the normal state as, for example, illustrated in FIG. 9A, a central portion 922 (see FIG. 9E and 9F) of flexible diaphragm 920 blocks an exit end 942 of second inlet port 940. A peripheral or outside portion 924 (see FIGS. 9D and 9F) of flexible diaphragm 920 blocks an opening 962 (see, for example, FIG. 9F) between second inlet port 940 and outlet port 970. Fluid entering valve system 900 from first inlet port 930 is thus blocked from flowing to second inlet port 940 and therethrough to any fluid source or reservoir in fluid connection with second inlet port 940.

As illustrated in FIG. 9C, pressurized fluid entering second inlet port 940 via, for example, a second fluid path 980b (for example, flexible tubing) supplies a second fluid (for example, contrast) to second inlet port 940 and exerts pressure on a central portion 922 (see FIG. 9D) of flexible diaphragm 920. Central portion 922 of flexible diaphragm deforms to block exit end 932 of first inlet port 930. A further increase in pressure, results in deformation of peripheral portion 924 of flexible diaphragm 920 as illustrated in FIG. 9D. Fluid entering, second fluid inlet 940 passes through passage 960 and passage 962 (see FIGS. 9D and 9F) to outlet port 970. Preferably, the pressure required to deform central portion 922 to block exit end 932 of inlet port 930 is less than the pressure required to deform peripheral portion 924 to open passage 962. Such an embodiment of flexible diaphragm 920 ensures that first inlet port 930 will be blocked before fluid from second inlet port 940 begins to flow through valve system 900, thereby ensuring that backmixing into first inlet port 930 is prevented. Diaphragm 920 can, for example, include a first material for central portion 922 and a second material for peripheral portion 924 to provide for different flexing forces/pressures. Alternatively, diaphragm 920 can be made of a single material and the thickness of central portion 922 can be less than the thickness of peripheral or outer portion 924 to provide for different flexing forces/pressures. Further, more than one flexible sealing member or diaphragm can be used. Preferably, different opening/flexing forces or pressures are provided ad described above. Use of a single flexible sealing member or diaphragm can, however, provide improved assembly efficiencies.

Figure 9F:
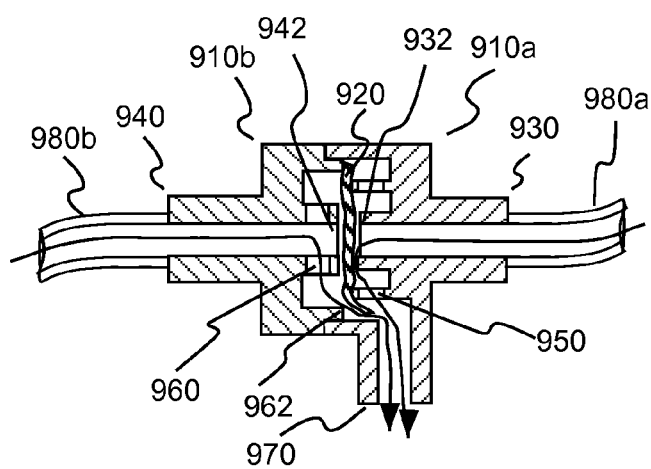
FIG. 9F illustrates the valve system of FIG. 9A in a state permitting simultaneous flow an mixing from both the first inlet port and the second inlet port.

FIG. 9F illustrates the valve system of FIG. 9A in a state permitting simultaneous flow an mixing from both the first inlet port and the second inlet port. In general, the pressures in first inlet 980*a*, second inlet 980*b* and outlet 970 are approximately equal in the dual flow mode.

FIGS. 10A-10D illustrate another embodiment of a valve system 1000 of the present invention which is connectible to a first fluid source and a second fluid source (for example, syringe 50*a* and syringe 50*b*), via a first inlet port 1010 and a second inlet port 1060, respectively. Valve system 1000 includes a check valve (for example, a flexible elastomeric disk) 1020 to control the fluid connection between first inlet port 1010 and outlet port 1070. A post 1030 biases flexible elastomeric disk 1020 in a closed position in which it blocks an exit 1012 of a passage leading to first inlet port 1010. A flexible diaphragm valve 1040 is also in fluid connection with first inlet port 1010. Flexible diaphragm valve does not allow fluid to pass in either direction, but operates to control the state of a passage 1050 in response to fluid pressure in first inlet port 1010. Outlet port 1070 delivers fluid from either or both of the inlet ports 1010 and/or 1060 to a patient.

In FIG. 10A, valve system 1000 is in its normal state, wherein fluid can flow from second inlet port 1060 to outlet port 1070 or from outlet port 1070 to second inlet port 1060 (for example, to perform a patency check). Fluid cannot flow into the first inlet port 1010 from second inlet port 1010 because elastomeric disk 1020 blocks end 1012 of inlet port 1010. As illustrated in FIG. 10B, as the pressure in first inlet port 1010 is increased, and at a pressure less than required to open elastomeric disk 1020 (for example, about 5 psi), diaphragm valve 1040 deforms to close passage 1050. As illustrated in FIG. 10C, as the pressure in first inlet port 1010 increases above the pressure required deform/open elastomeric disk 1020 fluid can flow from first inlet port 1010 to the outlet port 1070 (for example, this can occur at a pressures greater than 5 psi). In this state, no flow or mixing can take place in second inlet port 1060 because diaphragm valve 1040 closes passage 1050.

In FIG. 10D, fluid pressure in second inlet port 1060 is also increased. As the pressure in inlet port 1060 is increased to match the fluid pressure in first inlet port 1010, diaphragm valve 1040 returns to approximately its relaxed position, opening passage 1050 and allowing simultaneous flow from first inlet port 1010 and second inlet port 1060 to outlet port 1070. Because positive flow must be maintained, there cannot be upstream or backflow mixing (that is upstream of elastomeric disk 1020 into first inlet port 1010 and/or upstream of diaphragm valve 1040 into second inlet port 1060). As the pressure drops in either the first inlet port 1010 or second inlet port 1060, the respective valves will be closed.

Figure 11A:
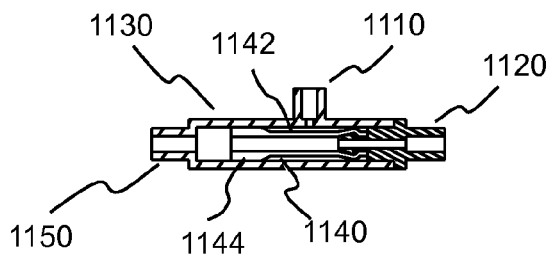
FIG. 11A illustrates another embodiment of a valve system of the present invention in a state to permit fluid connection between a second inlet port and an outlet port.

FIGS. 11A-11E illustrate another embodiment of a valve system 1100 of the present invention that is operable to control the flow between two fluid reservoirs to an outlet port 1150 and therethrough to a patient. A first inlet port 1110 is connected to a first reservoir, while a second inlet port 1120 is connected to a second reservoir, as described above. A valve body 1130 includes a tube valve member 1140 therein. Outlet port 1150 delivers fluid from either or both of the inlet ports 1110, 1120 to the patient. In FIG. 11A, the tube valve 1100 is in its normal state or flow condition in which fluid can flow from second inlet port 1120 to the outlet port 1150 (or in the reverse direction, for example, for a patency check). First inlet port 1110 is blocked by flexible tube member 1140, so there can be no backmixing into first inlet port 1110.

Figure 11B:
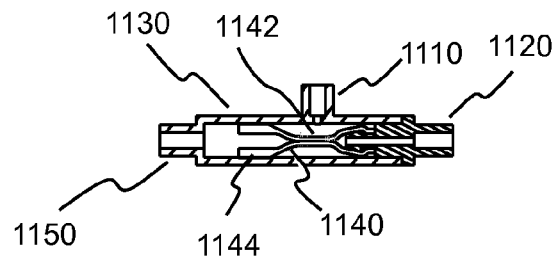
FIG. 11B illustrates the valve system of FIG. 11A in a state preventing flow from either the first or second inlet port to the outlet port.

In FIG. 11B, the pressure in first inlet port 1110 is increased. At a relatively low pressure, a central, relatively thin-walled section 1142 of tube valve member 1140 squeezes closed, blocking second inlet port 1120. In the state illustrated in FIG. 11B, the pressure is not high enough to cause fluid from first inlet port 1110 to flow between thicker end section 1144 of tube valve member 1140 and an inner wall of valve body 1130 to reach outlet port 1150.

Figure 11C:
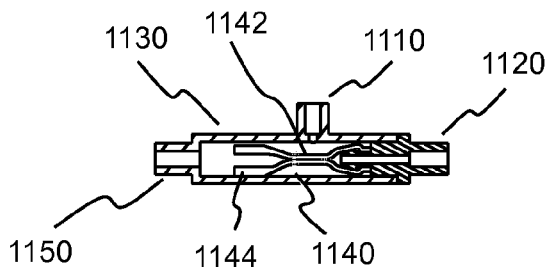
FIG. 11C illustrates the valve system of FIG. 11A in a state permitting flow from the second inlet port to the outlet port.

In FIG. 11C, a slightly higher pressure in the first inlet port 1110 causes relatively thicker section 1144 of tube valve member 1140 to partially collapse to provide an open volume between thicker section 1144 and valve housing 1130 to allow flow from first inlet port 1110 to outlet port 1150. In the state illustrated in FIG. 11C, second inlet port 1120 remains blocked by fully collapsed central section 1142 of tube valve member 1140.

Figure 11D:
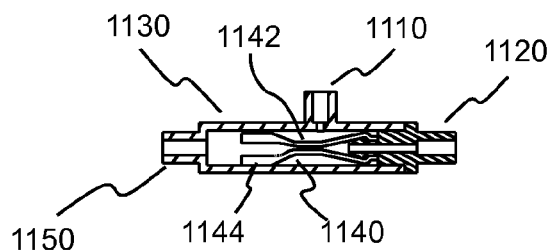
FIG. 11D illustrates the valve system of FIG. 11A in a state to permit simultaneous flow and mixing from both inlet ports.
Figure 11E:
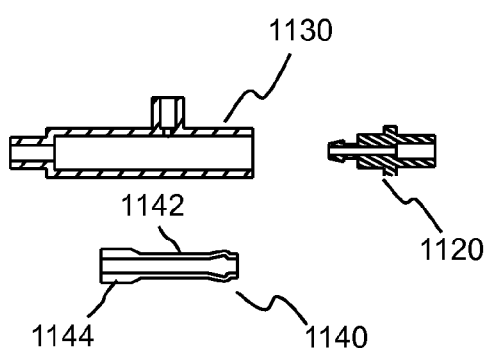
FIG. 11E illustrates the valve system of FIG. 11A in a disassembled state.

In FIG. 11D, both first inlet port 1110 and second inlet port 1120 are pressurized. In this state, flow through the tube valve 1100 from first inlet port 1110 occurs as described above. However, the increase in pressure in second inlet port 1120 causes central section 1142 of tube valve member to partially open to allow flow from second inlet port 1120 to outlet port 1150, thereby allowing simultaneous flow from both inlet ports 1110 and 1120. If flow from either inlet ports 1110 or 1120 is ceased, tube valve member 1140 closes the fluid path to the other inlet port to prevent reverse mixing upstream.

The foregoing description and accompanying drawings set forth the preferred embodiments of the invention at the present time. Various modifications, additions and alternative designs will, of course, become apparent to those skilled in the art in light of the foregoing teachings without departing from the scope of the invention. The scope of the invention is indicated by the following claims rather than by the foregoing description. All changes and variations that fall within the meaning and range of equivalency of the claims are to be embraced within their scope.

What is claimed is:

1. A valve system for use in a system comprising a first source of a first pressurized fluid and a second source of a second pressurized fluid, the valve system comprising:

a valve housing comprising a first inlet port adapted to be placed in fluid connection with the first source, a second inlet port adapted to be placed in fluid connection with the second source and an outlet port; and a backflow prevention system comprising a deformable sealing member having a first portion and a second portion, the deformable sealing member biased to prevent flow of the first pressurized fluid through the second inlet and to prevent flow of the second pressurized fluid through the first inlet port, wherein the valve system is adapted to provide a fluid path between at least the first inlet port and the outlet port to enable fluid to be drawn from the outlet port to the first inlet port, and further wherein flow of the second pressurized fluid into the second inlet port at a first pressure deforms the first portion of the sealing member to block flow into the first inlet port and flow of the second pressurized fluid into the second inlet port at a second pressure higher than the first pressure deforms the second portion of the sealing member to open a fluid path between the second inlet port and the outlet port.

2. The valve system of claim 1 wherein the valve housing comprises a first housing member comprising the first inlet port and a second housing member comprising the second inlet port, the first housing member and the second housing member being attached to form the valve housing, the deformable sealing member being positioned between the first housing member and the second housing member.

3. The valve system of claim 1 wherein flow of the first pressurized fluid into the first inlet port and concurrent flow of the second pressurized fluid into the second inlet port causes flow from the first inlet port into the outlet port and concurrent flow from the second inlet port into the outlet port.

4. The valve system of claim 1 providing for flow from the first inlet port to the outlet port and concurrent flow from the second inlet port to the outlet port.

5. The valve system of claim 1 wherein the first portion of the deformable sealing member comprises a central portion and the second portion of the deformable sealing member comprises a peripheral portion.

6. An injection system comprising:
a first source of a first pressurized fluid;
a second source of a second pressurized fluid, and
a valve system comprising:
a valve housing comprising a first inlet port in fluid connection with the first source, a second inlet port in fluid connection with the second source and an outlet port; and
a backflow prevention system comprising a deformable sealing member having a first portion and a second portion, the deformable sealing member biased to prevent flow of the first pressurized fluid through the second inlet and to prevent flow of the second pressurized fluid through the first inlet port,
wherein the valve system is adapted to provide a fluid path between at least the first inlet port and the outlet port to enable fluid to be drawn from the outlet port to the first inlet port, and further wherein flow of the second pressurized fluid into the second inlet port at a first pressure deforms the first portion of the sealing member to block flow into the first inlet port and flow of the second pressurized fluid into the second inlet port at a second pressure higher than the first pressure deforms the second portion of the sealing member to open a fluid path between the second inlet port and the outlet port.

7. The injection system of claim 6 wherein the first source is a first syringe in fluid connection with a powered injector and the second source is a second syringe in fluid connection with the powered injector.

8. The injection system of claim 6 wherein the first portion of the deformable sealing member comprises a central portion and the second portion of the deformable sealing member comprises a peripheral portion.

9. A valve system for use in a system comprising a first source of a first pressurized fluid and a second source of a second pressurized fluid, the valve system comprising:
a valve housing comprising a first inlet port adapted to be placed in fluid connection with the first source, a second inlet port adapted to be placed in fluid connection with the second source and an outlet port;
at least one deformable sealing member having a central portion and an outer portion, the at least one deformable sealing member in operative connection with the first inlet port and the second inlet port, the at least one deformable sealing member being biased to block flow into the second inlet port, and
wherein the valve system is adapted to provide a fluid path between the first inlet port and the outlet port, and further wherein flow of the second pressurized fluid into the second inlet port at a first pressure deforms the central portion of the sealing member to block flow into the first inlet port and further wherein flow of the second pressurized fluid into the second inlet port at a second pressure, higher than the first pressure, deforms the outer portion of the sealing member to open a fluid path between the second inlet port and the outlet port.

10. The valve system of claim 9 wherein flow of the first pressurized fluid into the first inlet port and concurrent flow of the second pressurized fluid into the second inlet port deforms the central portion of the deformable sealing member and causes flow from the first inlet port into the outlet port and concurrent flow from the second inlet port into the outlet port.

11. The valve system for claim 9 wherein the valve housing comprises a first housing member comprising the first inlet port and a second housing member comprising the second inlet port, the first housing member and the second housing member being attached to form the valve housing, the deformable sealing member being positioned between the first housing member and the second housing member.

12. The valve system for claim 9 wherein the valve housing comprises a first housing member and a second housing member that are attachable to form the valve housing comprising the first inlet port, the second inlet port and the outlet port, the deformable sealing member being positioned between the first housing member and the second housing member.

* * * * *

UNITED STATES PATENT AND TRADEMARK OFFICE
CERTIFICATE OF CORRECTION

PATENT NO. : 7,475,701 B2
APPLICATION NO. : 11/420094
DATED : January 13, 2009
INVENTOR(S) : Trocki Page 1 of 1

It is certified that error appears in the above-identified patent and that said Letters Patent is hereby corrected as shown below:

IN THE SPECIFICATION

Column 2, Line 5, after "check" insert -- . --.

IN THE CLAIMS

Column 16, Line 10, delete "deforrnable" and insert -- deformable --, therefor.

Signed and Sealed this

Third Day of March, 2009

JOHN DOLL
*Acting Director of the United States Patent and Trademark Office*